United States Patent [19]

Conston et al.

[11] Patent Number: 5,456,693
[45] Date of Patent: Oct. 10, 1995

[54] EMBOLIZATION PLUGS FOR BLOOD VESSELS

[75] Inventors: Stanley R. Conston, San Carlos; Gregory S. Dapper, Newark; Aileen L. Murphy, Menlo Park; Jennifer Raeder-Devens, Oakland; Ronald Yamamoto, San Francisco, all of Calif.

[73] Assignee: Vitaphore Corporation, Plainsboro, N.J.

[21] Appl. No.: 297,271

[22] Filed: Aug. 25, 1994

Related U.S. Application Data

[63] Continuation of Ser. No. 948,235, Sep. 21, 1992, abandoned.

[51] Int. Cl.⁶ ........................................ A61L 15/00
[52] U.S. Cl. ................... 606/192; 514/773; 128/DIG. 8
[58] Field of Search ........................... 604/11, 55, 368, 604/369; 128/831, 843, 899, DIG. 8; 606/191–194, 154; 514/801, 773

[56] References Cited

U.S. PATENT DOCUMENTS

| | | | |
|---|---|---|---|
| 4,365,621 | 12/1982 | Brundin | 606/191 |
| 4,509,504 | 4/1985 | Brundin | 128/899 |
| 4,537,186 | 8/1985 | Verschoof et al. | 128/831 |
| 4,582,640 | 4/1986 | Smestad et al. | 128/DIG. 8 |
| 4,703,108 | 10/1987 | Silver et al. | 128/DIG. 8 |
| 4,749,689 | 6/1988 | Miyata et al. | 128/DIG. 8 |

OTHER PUBLICATIONS

Carlos E. Encarnacion, et al.: "Subselective Embolization with Gelatin Sponge through an Open–ended Guide Wire", Radiology, vol. 174, No. 1, p. 265 (1990).

A. H. Matsumoto, P. V. Suhocki, and K. H. Barth: "Super-selective Gelfoam Embolotherapy Using a Highly Visible Small Caliber Catheter", Cardio Vascular and Interventional Radiology (1988) vol. 11, 303–306.

K. H. Barth, J. D. Strandberg, and R. I. White: "Long Term Follow-Up of Transcatheter Embolization With Autologous Clot, Oxycel and Gelfoam in Domestic Swine", Investigative Radiology (1977) vol. 1, 273.

A. Berenstein and E. Russell: "Gelatin Sponge in Therapeutic Neuroradiology": Neuroradiology (1981) vol. 141, 105–112.

*Primary Examiner*—Stephen C. Pellegrino
*Assistant Examiner*—William Lewis
*Attorney, Agent, or Firm*—Fish & Richardson

[57] ABSTRACT

A bioresorbable and hemostatic plug for embolization made from a collagen piece is compressed so as to be longitudinally insertable into a tubular biological vessel such as a blood vessel to be occluded. The collagen piece is capable of expanding radially inside the vessel by absorbing fluid such as the blood and thereby providing mechanical fixation in and occlusion of the vessel. Two such collagen pieces may be used with a spacer of a different material in between. Different kinds of therapeutic agents can be bonded to or physically absorbed by the collagen pieces so as to be delivered to the site of occlusion.

21 Claims, No Drawings

EMBOLIZATION PLUGS FOR BLOOD VESSELS

This is a continuation of application Ser. No. 07/948,235, filed Sep. 21, 1992, to be abandoned.

BACKGROUND OF THE INVENTION

This invention relates to plugs for embolization of a biological vessel and, more particularly, to biodegradable collagen plugs which may be placed inside a blood vessel for occlusion.

There is a great variety of clinical situations where blood vessels must be blocked, such as when bleeding in the brain needs to be controlled or when the blood supply to tumorous tissues must be blocked. Other examples of situations requiring permanent or temporary embolization include, but are not limited to, occlusion of saphenous vein side branches in a saphenous bypass graft procedure, neurovascular occlusion, chemoembolization, aortic aneurysm correction procedure, chronic venous insufficiency treatment, and renal embolization.

Various means have been used in these applications to occlude blood vessels, such as by advancing a small diameter catheter from a distant vessel, inflating a small rubber balloon at the end of the catheter to mechanically wedge it into place in order to block the vessel, and thereafter withdrawing the catheter. A disadvantage of this method is that the rubber balloon may become dislodged at a later time and become life-threatening as a free-floating embolus. Another procedure is to inject at the desired site in the blood vessel a suspension of collagen with clotting factors, thereby inducing an embolus. The clots will be re-absorbed with time, alleviating the risk of a free-floating embolus. This procedure, however, is not desirable when precise location of the embolus is desired because the clotting must be induced sufficiently rapidly such that the clot can be prevented from moving downstream to an undesired location or from forming microemboli before attaching to the blood vessel walls. Still another procedure, which has been suggested, is to use a syringe to inject through a catheter a liquid suspension of Gelfoam (registered trademark of Upjohn) particles or small "piedgets". While Gelfoam, manufactured from animal gelatin, has a sponge-like consistency when wet, the use of a syringe to inject suspended particles into a catheter limits the compression of the particles and the resultant mechanical fixation in-situ of the embolizing material.

It is therefore an object of the present invention to provide an occluding material (hereinafter broadly referred to as a plug) for creating a rapidly clotting, mechanically stable, bioresorbable embolus in a controlled vascular embolization process.

It is another object of the present invention to provide such a plug that can create such an embolus at a predetermined location within a blood vessel such as a branch from the saphenous vein.

It is still another object of the present invention to provide such a plug that can also deliver various active agents such as antibiotics to a specified site inside such a vessel.

Thus, the issues which are critical to the plug design include chemical, mechanical and biological interactions of the material with the vein and blood. In certain applications, it may be desirable that the plug material can occlude a flow permanently, and be replaced by native tissue. In other applications such as chemoembolization of the hepatic artery, on the other hand, temporary occlusion may be preferred, allowing the material to erode gradually and normal flow restored in the vessel. It is therefore still another object of the present invention to provide a plug made from a material of which the rate of bioerosion can be controlled.

SUMMARY OF THE INVENTION

A plug embodying the present invention with which the above and other objects can be accomplished may be characterized as comprising one or two pieces of collagen material which is flexible and deformable, like sponge, such that it can be compressed to be inserted into a tubular biological vessel such as a blood vessel, but can also absorb fluid, after it is inserted into such a vessel, to expand so as to provide mechanical fixation inside the vessel and also to block the flow of fluid such as blood through the vessel. The sponge-like material may comprise cross-linked collagen and may contain antibiotics or other kinds of drugs which may be desirable at the position of the vessel where the plug is deposited. Such a plug may be not only biodegradable but also significantly hemostatic, and may also have the property of promoting tissue ingrowth.

A plug of another kind according to the present invention may be comprised of two such collagen pieces separated from each other by a spacer, or a bolus, in between. The spacer may comprise sclerosing, clotting and other agents. Such a plug can serve not only to occlude the vessel but also as a carrier of drugs.

DETAILED DESCRIPTION OF THE INVENTION

A plug according to a first embodiment of the present invention may be characterized simply as being a single piece made from a collagen material. A collagen plug material is preferred because of its tissue compatibility and bioabsorption over time. It is also a very versatile material which can be formulated into a sponge, a film or a clear viscoelastic fluid, depending on the steps used in the processing. Collagen has some attractive chemical properties in vivo, such as being hemostatic, being chemotactic and encouraging fibroblast ingrowth. In implantation studies, it can provide a scaffold for healing deep wounds and formation of new tissue.

The collagen material, from which a plug embodying the present invention is made, may be of almost any commercially available type. It may preferably be from a processed animal source such as bovine corium (hide), bovine tendon and porcine skin. Reprocessed insoluble collagen from animal sources is commercially available in the form of sponges or non-woven webs. The collagen is formed into the shape of plugs of appropriate size to be determined by the intended application. In an area of low venous throughput for temporary occlusion of blood flow, for example, a plug which is not too much larger than the inner diameter of the vessel should suffice. For applications demanding permanent occlusion of vessels subjected to arterial pressures, on the other hand, a plug of higher compression modulus and larger expanded size relative to the inner diameter of the lumen will be necessary. The shape of the plug can also be tailored to fit the need of a given application. A spherical, cylindrical, conical or rolled plug may be appropriate for any given application.

The plugs can be molded or fabricated otherwise, and compressed into a given shape. Typically, the plugs are compressed sufficiently so that their diameter is smaller than the lumen for ease of insertion. In general, such configurations that allow the most collagen to be inserted into the lumen are most beneficial. Sponge-like porous plugs with pore diameters greater than 50 microns are preferred for promoting cellular ingrowth. A dry, highly compressed collagen plug like this fully hydrates and expands to several times its compressed size within a short period of time upon contact with bodily fluid, thereby tightly affixing itself to a particular location within a blood vessel.

The plug according to the present invention may be made from Collastat® Hemostatic Sponge (Vitaphore Corp.) Use may also be made of Vitacol™ (proprietary collagen of the assignee herein, very similar to Collastat in form and function), Semex Collagen Powder (Semex Medical, Inc.), etc. The crosslinking agent may be formaldehyde vapor (FMV), glutaraldehyde or other agents familiar to those skilled in the art. Crosslinking effectively increases the strength (compression modulus) of the material, and slows its bioerosion in vivo. Crosslinked collagen materials with shrink temperature ($=T_s$) greater than 55° C. and with a modulus at 60% volumetric compression of greater than 0.15 g/mm$^2$ are particularly preferred.

Use may also be made of medical grade polyurethane foams such as Hypol (W. R. Grace & Co.) The urethane foams have very good memory characteristics and a higher compression modulus in water than a collagen sponge of similar solids content. Polyurethane plugs may be either impregnated with collagen or combined with aqueous collagen slurry in a foam-forming step. Plugs which are imbibed with collagen post foam-forming may be lightly crosslinked with formaldehyde vapor. The plug is normally formed cylindrically or as a composite in anticipation that a higher surface contact area will inhibit movement of the plug under arterial pressure. It is noteworthy that the bioresorption time of the plug can be controlled in part by varying the length of the plug, its bulk density, as well as the extent of crosslinking.

The environment surrounding a formed or forming thrombus influences its resolution. In the presence of flowing blood, the thrombus is in a state of flux with fresh platelets being deposited on the periphery, undergoing degranulation and thrombus enlargement. On the other hand, the flow of blood can dislodge weakly bound aggregates of platelets, thereby reducing the immediate size of the thrombus. In static blood, such as between two plugs, the number of platelets is fixed; whatever aggregation, degranulation and fibrin crosslinking that is going to take place will take place within 15 to 30 minutes after formation. From that point on, the thrombus will start to become remodeled by the action of plasmin and other proteases as well as by the invasion of migratory cells. In other words, resolution of the thrombus formed after placement of a single plug will be different from the resolution of the thrombi after placement of two plugs with a space therebetween. In the former configuration, fibroblast invasion and eventual blockage by replacement tissue will compete with the other processes as the thrombus is in a state of flux with access to fresh platelets. In the latter configuration, the two plugs are separated, permitting development of a solid tissue mass while protected from interference from the flux of blood. Thus, a plug according to a second embodiment of the present invention may be characterized as having two collagen pieces as described above and a spacer, or a bolus, of another material which is disposed between them for serving to separate them from each other. This material will remain localized between the two plug pieces for a desired period of time. A derivative of this two-piece design can include placement of an active agent into the space between the two plug pieces. This design can be optimized to manipulate the healing process. One embodiment of the plug assembly according to the invention involves insertion of a hyperosmotic agent spacer between the two plugs. The transient shock to the lumen of the vessel in the surrounding area could induce prolonged inflammation and enhance tissue fibrosis. Examples of such material include concentrated salts or low molecular weight (such as less than 2000) polyethylene glycol which can act as a dehydrating agent at the occlusion site, influencing tissue remodeling. A bolus of radiopaque material held between the two plug pieces will allow direct visualization of the occlusion site several days after surgery without the need for interventional techniques.

Another aggressive method of compromising the lumen in the space between the two plug pieces is by introduction of surface active agents or alcohols into the spacer capsule. An alcohol may serve as a dehydrating agent, again compromising the cells and encouraging inflammation and the wound healing process. A surface active agent will effectively destroy the epithelial layer, inducing inflammation and wound healing as above. Examples of surfactive agents include sodium tetradecyl sulfate and morrhuate sodium. This effect will probably be more prolonged than the osmotic and dehydration methods explained above.

Although the plug pieces according to the present invention are primarily for occluding a tubular biological vessel such as a blood vessel, they can also themselves provide supporting chemotherapy to the site of occlusion by delivering various active agents to the site. In other words, the collagen plugs according to the present invention may be pretreated with desirable clinical or therapeutic drugs such as clotting factors, tissue attachment factors, chemotherapeutic agents, and anti-neoplastic agents. Thus, for example, chemotherapeutic agents may be slowly delivered to tissues downstream from the plug as the plug is bioresorbed. Fixation of drugs or other factors to the collagen structure may be carried out by a variety of known methods, such as by treating the collagen with a solution of the drug or factor prior to drying and compressing the plug. The drugs or factors may be covalently bonded, ionically or hydrophobically bonded, or merely physically absorbed into the collagen, depending upon the desired delivery profile of the drug because the mode of drug incorporation into the plug piece determines the release rate of the agent. Drugs or factors which are only physically absorbed into the collagen will be almost instantaneously releasable as a bolus into the blood stream upon first contact with the blood, whereas drugs or factors which are covalently bonded to the collagen will be released over a prolonged period of time in proportion with the time and degree of bioresorption of the collagen itself. Examples of active agents that may thus be incorporated include (1) antibiotics such as tobramycin, gentamycin, and vancomycin; (2) clotting factors such as Factors I–VIII, thrombin and fibrinogen; (3) tissue attachment factors such as vitronectin, fibronectin and laminin; (4) protease inhibitors such as aprotinin and ethylenediaminetetraacetate (EDTA); (5) anti-neoplastic agents such as 5-fluorouracil, methotrexate, nitroso-ureas, cisplatin, cyclophosphamide, dacarbazine, dactinomycin, doxorubicin, etoposide, mitomycin, vinblastine, and vindesine; and (6) sclerosing agents such as morrhuate sodium, ethanolamine oleate, and tetradecyl sulfate.

EXPERIMENTAL RESULTS

In what follows, there will be described results of vascular occlusion experiments on animals with collagen plugs according to the present invention. In all these experiments, plugs were designed to occlude a vessel by occupying its full cross-section and exerting sufficient radial pressure and friction on its wall to remain in place even when subjected to systolic pressures. All of the collagen plugs were fabricated by casting various concentrations of collagen solutions, typically 0.75 to 2.0 weight %, into spherical molds or flat molds from which cylindrical plugs could be punch cut. The collagen solutions were lyophilized to form sponges and then crosslinked by exposure to formaldehyde vapor to achieve the desired shrink temperature.

Experiment 1: The feasibility of occlusion of flow was tested by inserting spherical collagen plugs into the rabbit auricular artery. Spherical plugs of 1.4 to 2.1 mm in diameter were compressed in the dry state and inserted into a 20-gauge cannula with an internal diameter of 0.55 mm. In doing so, the external radial dimensions of the plugs were reduced by a factor (that is, a compression in the critical aspect) of 2.5 to 3.8 from the original unconstrained condition so as to be insertable into the cannula lumen. The cannula was inserted into the auricular artery and the plug released with the aid of a flexible metal plunger. The plugs began to swell and were immediately fixed into position, initiating clotting and occluding flow.

Experiment 2: In this experiment, the effect of plug composition was explored in the rabbit auricular artery model. Cylindrical collagen plugs ($T_s$=70°–83° C. with modulus at 60% volumetric compression=2.55 g/mm$^2$) and urethane/collagen (Hypol) composite plugs (Moduli at 60% volumetric compression= 1.31–15.32 g/mm$^2$) of 1.8 mm in diameter were fabricated. These plugs were compressed in the dry state to fit a 20-gauge cannula, giving a compression ratio of 3.3 in the critical aspect. The plugs were inserted into the artery as done in Experiment 1 and monitored for 30 days. In 30 days, the high density collagen plug resorbed, and the artery was not occluded. With the exception of one totally occluded ear, the urethane composite plugs were partly to fully resorbed, with urethane fragments still present in the lumen. These arteries showed flow returning through the artery due to recanalization.

Experiment 3: In this experiment, the effect of plug composition was explored in the rabbit auricular artery model. Cylindrical collagen plugs of two densities ($T_s$= 58°–67° C. with modulus at 60% volumetric compression= 0.08 g/mm$^2$ and $T_s$=82°–87° C. with modulus at 60% volumetric compression=3.35 g/mm$^2$) and urethane/collagen (Hypol) composite plugs of 1.63 mm in diameter were fabricated. The plugs were compressed in the dry state to a compression ratio of 3.0 in the critical aspect. The plugs were inerted into the artery and monitored for 42 days. By 42 days, only the artery with the high density collagen plug was occluded.

Experiment 4: In this experiment, the effect of single versus multiple plug insertion was explored in the rabbit auricular artery model. High density cylindrical collagen plugs ($T_s$=82°–87° C. with modulus at 60% volumetric compression=3.35 g/mm$^2$) of 1.37 mm in diameter were fabricated, to give a compression ratio of 2.5 in the critical aspect. The plugs were inserted into the artery singly, doubly with a space between them, or doubly with a 3–5 μl bolus of polyethylene glycol (molecular weight 1000) between them. At 120 days, none of the single plugs fully occluded flow, all of the double plugs with space were occluded, and 75% of the double plugs with PEG 1000 bolus were fully occluded.

Although the present invention has been described above by way of only a limited number of embodiments and examples, they are intended to be merely illustrative, and not as limiting the scope of the invention. Many modifications and variations are possible within the spirit of the present invention. Such modifications and variations that may be apparent to a person skilled in the art are intended to be included within the scope of the invention.

What is claimed is:

1. A plug which, in a compressed condition, is longitudinally insertable into a tubular biological vessel, said plug comprising a piece having unconstrained dimension greater than the inner diameter of said vessel, said piece having a modulus at 60% compression greater than 0.15 g/mm$^2$ and being capable of expanding radially inside said vessel by absorbing fluid and thereby providing mechanical fixation in and occlusion of said vessel.

2. The plug of claim 1 wherein said piece comprises collagen.

3. The plug of claim 1 wherein said piece is porous, having pores with diameters greater than 50 microns, said piece being capable of promoting cellular ingrowth.

4. The plug of claim 1 wherein said piece comprises cross-linked collagen with shrink temperature higher than 55° C.

5. The plug of claim 1 wherein said piece comprises crosslinked collagen with modulus at 60% volumetric compression greater than 1.3 g/mm$^2$.

6. The plug of claim 1 wherein said piece contains one or more active agents selected from the group consisting of sclerosing agents, clotting agents, hyperosmotic agents, surface active agents, antibiotics, tissue attachment factors, protease inhibitors, and anti-neoplastic agents.

7. The plug of claim 6 wherein said one or more active agents are covalently, ionically or hydrophobically bound to said piece.

8. The plug of claim 6 wherein said one or more active agents are physically absorbed by said piece.

9. The plug of claim 6 wherein said hyperosmotic agents include polyethylene glycol with molecular weight less than 2000, said sclerosing agents include morrhuate sodium, ethanolamine oleate, and tetradecyl sulfate, said clotting agents include Factors I–VIII, thrombin and fibrinogen, said antibiotics include tobramycin, gentamycin and vancomycin, said tissue attachment factors include vitronectin, fibronectin and laminin, said protease inhibitors include aprotinin and ethylenediaminetetraacetate, and said anti-neoplastic agents include 5-fluorouracil, methotrexate, nitroso-ureas, cisplatin, cyclophosphamide, dacarbazine, dactinomycin, doxorubicin, etoposide, mitomycin, vinblastine, and vindesine.

10. The plug of claim 1 wherein said piece can be compressed from its unconstrained state such that its external radial dimensions can be reduced by a factor of at least 2.5.

11. The plug of claim 1 comprising two pieces made from collagen and a spacer disposed between said two pieces, said pieces being each capable of expanding radially inside said vessel by absorbing fluid and thereby providing mechanical fixation in and occlusion of said vessel.

12. The plug of claim 11 wherein said pieces have unconstrained dimension greater than the inner diameter of said vessel and are in compressed condition before said plug is inserted into said vessel.

13. The plug of claim 11 wherein said pieces are porous, having pores with diameters greater than 50 microns, said pieces being capable of promoting cellular ingrowth.

14. The plug of claim 11 wherein said plug comprises bioerodible material with a controllable rate of bioresorption.

15. The plug of claim 11 wherein said pieces comprise crosslinked collagen with shrink temperature higher than 55° C.

16. The plug of claim 11 wherein said pieces comprise crosslinked collagen with modulus at 60% volumetric compression greater than 1.3 g/mm².

17. The plug of claim 11 wherein said spacer contains one or more active agents selected from the group consisting of sclerosing agents, clotting agents, hyperosmotic agents, surface active agents, antibiotics, tissue attachment factors, protease inhibitors, anti-neoplastic agents and a radiopaque material.

18. The plug of claim 17 wherein said one or more active agents are covalently, ionically or hydrophobically bound to said piece.

19. The plug of claim 17 wherein said one or more active agents are physically absorbed by said piece.

20. The plug of claim 17 wherein said hyperosmotic agents include polyethylene glycol with molecular weight less than 2000, said sclerosing agents include morrhuate sodium, ethanolamine oleate, and tetradecyl sulfate, said clotting agents include Factors I–VIII, thrombin and fibrinogen, said antibiotics include tobramycin, gentamycin and vancomycin, said tissue attachment factors include vitronectin, fibronectin and laminin, said protease inhibitors include aprotinin and ethylenediaminetetraacetate, and said anti-neoplastic agents include 5-fluorouracil, methotrexate, nitroso-ureas, cisplatin, cyclophosphamide, dacarbazine, dactinomycin, doxorubicin, etoposide, mitomycin, vinblastine, and vindesine.

21. A plug which is compressible and is longitudinally insertable into a tubular biological vessel when in a compressed condition, said plug comprising a piece having unconstrained dimension greater than the inner diameter of said vessel, said piece comprising bioerodible material with a controllable rate of bioresorption, having a modulus at 60% compression greater than 0.15 g/mm² and being capable of expanding radially inside said vessel by absorbing fluid and thereby providing mechanical fixation in and occlusion of said vessel.

* * * * *

UNITED STATES PATENT AND TRADEMARK OFFICE
CERTIFICATE OF CORRECTION

PATENT NO.   : 5,456,693

DATED        : October 10, 1995

INVENTOR(S): Stanley R. Conston, Gregory S. Dapper, Aileen L. Murphy, Jennifer Raeder-Devens and Ronald Yamamoto It is certified that error appears in the above-identified patent and that said Letters Patent is hereby corrected as shown below:

Column 1, line 43:   change "piedgets" to --pledgets--.

Signed and Sealed this

Seventeenth Day of September, 1996

Attest:

BRUCE LEHMAN

Attesting Officer   Commissioner of Patents and Trademarks